United States Patent [19]

Tøpholm

[11] Patent Number: 4,585,089

[45] Date of Patent: Apr. 29, 1986

[54] COUPLING ELEMENT FOR A HEARING AID

[75] Inventor: Christian Tøpholm, Verløse, Denmark

[73] Assignee: Topholm & Westerman I/S, Verlose, Denmark

[21] Appl. No.: 694,401

[22] PCT Filed: May 15, 1984

[86] PCT No.: PCT/DK84/00038

§ 371 Date: Jan. 4, 1985

§ 102(e) Date: Jan. 4, 1985

[87] PCT Pub. No.: WO84/04645

PCT Pub. Date: Nov. 22, 1984

[30] Foreign Application Priority Data

May 16, 1983 [DK] Denmark ............................ 2171/83

[51] Int. Cl.[4] ................................................ A61B 7/02

[52] U.S. Cl. .................................... 181/135; 181/130; 179/107 E

[58] Field of Search ............................... 181/130, 135; 179/107 E

[56] References Cited

U.S. PATENT DOCUMENTS

| | | | |
|---|---|---|---|
| 2,325,590 | 8/1943 | Carlisle et al. | 179/107 E |
| 4,069,400 | 1/1978 | Johanson et al. | 179/107 E |
| 4,375,016 | 2/1983 | Harada | 181/135 X |
| 4,381,830 | 5/1983 | Jelowek et al. | 181/130 X |

FOREIGN PATENT DOCUMENTS 823214 11/1955 United Kingdom .

*Primary Examiner*—Benjamin R. Fuller
*Attorney, Agent, or Firm*—Lewis H. Eslinger

[57] ABSTRACT

A coupling element for establishing acoustic connection between a cylindrical hearing aid placed in the concha and a custom made ear plug placed in the auditory canal is formed by a disc-shaped element, which can be rotatably mounted a sound exit nipple on the hearing aid and an angularly bent tube section rotatably mounted on a laterally directed spout on the disc-shaped part. Because the hearing aid housing can rotate about its own axis in the concha and the coupling element can rotate about the nipple of the hearing aid, and because the tube section can rotate about the spout of the disc-shaped part, the tube section may be placed with respect to the auditory canal such that the sound channel in the ear plug can be established by a single, straight bore.

1 Claim, 5 Drawing Figures

COUPLING ELEMENT FOR A HEARING AID

Figure 1:
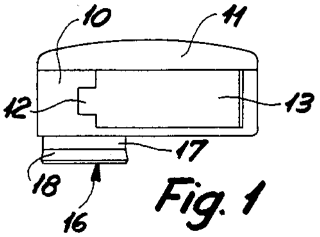

The progressive component miniaturization has led to the development of hearing aid structures which are so small that the entire aid can be placed in the cavity called concha, which is defined by various projecting parts of the outer ear. The first aids of this type were manufactured in that a hollow ear plug was made on the basis of a mould of the outer ear, configured to fit the ear in question and having a part which was formed with a sound channel extending through it and which protruded somewhat into the auditory canal, and then the components of the aid were inserted into the ear plug, which was finally provided with a cover. Such an extensive adaptation made the manufacturing process time-consuming and expensive.

It is known to simplify and reduce the cost of hearing aids to be positioned in the outer ear by incorporating the components in an aid housing, which is then placed in a recess adapted to the shape of the housing and provided in a custom made ear plug.

It is also known to form the aid housing as a cylinder and to place the sound exit aperture in the vicinity of the periphery on the inwardly directed end face so that the housing can rotate with respect to the ear plug in order for the sound exit to be positioned as appropriately as possible with respect to the auditory canal. However, it has been found that the position of the auditory canal with respect to the concha varies so widely that it is often necessary in practice to drill two angularly meeting holes in the ear plug to form a sound channel establishing acoustic connection between the sound exit of the hearing aid and the auditory canal. The U.S. Pat. No. 4,069,400 shows a substantially triangular hearing aid housing with a coupling element removably placed on an edge face and forming a sound exit spout. The availability of a plurality of different coupling elements with spouts pointing in different directions enables some adaptation to individual anatomic conditions; however, nor is this variational facility sufficient to ensure that complicated drilling in the ear plug can always be avoided.

The invention relates to a coupling element of the type stated in the introductory portion of the claim, and its object is to provide such a coupling element which facilites adaptation of a hearing aid to the user's ear by providing the greatest possible positional freedom at the end of a sound channel connected with the sound exit nipple of the aid.

This is achieved in that the coupling element is constructed as stated in the characterizing portion of the claim; in addition to rotation of the entire hearing aid about its own axis which is made possible by the preferred cylindrical shape, known per se, of the hearing aid and which determines the position of the nipple, the structure enables:

(1) rotation of the coupling element around the sound exit nipple, thereby determining a certain region for the position of the sound exit, and (2) rotation of the tube section around the spout, thereby determining the orientation of the tube section and the final position of the sound exit.

These adjusting possibilities ensure that the sound exit can always be placed so that connection to the sound channel can be obtained by a single, straight bore through the ear plug.

Figure 2:
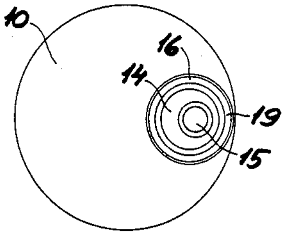
Figure 3:
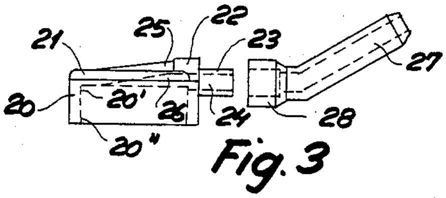
Figure 4:
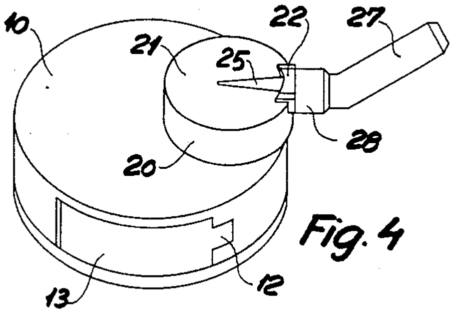
Figure 5:
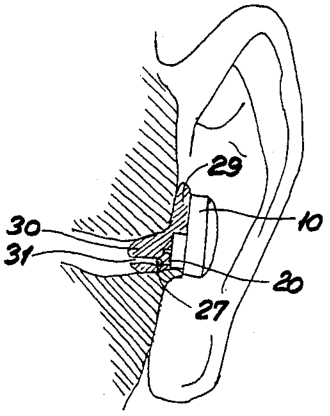

The invention will be explained more fully below with reference to the drawing, in which FIGS. 1 and 2 are enlarged views of a substantially cylindrical hearing aid housing, seen in a direction toward an edge face and from the inner side, respectively, FIG. 3 is an enlarged side view of an embodiment of the coupling element of the invention, in a disassembled state, FIG. 4 is a perspective view of the coupling element applied to the hearing aid housing of FIGS. 1 and 2, and FIG. 5 is a section through an outer ear, in which an ear plug and a hearing aid as well as a coupling element of the invention are positioned.

In FIGS. 1 and 2, 10 designates a relatively flat cylindrical hearing aid housing, whose front 11 is formed by a rotary botton for volume control and for actuating a switch (not shown). A battery drawer 13 is pivotally mounted in the edge face of the housing by means of a hinge 12. On the inner side, the housing has a sound exit spout 14 with a sound exit opening 15 disposed in the vicinity of the periphery. This spout is surrounded by a snap fastener means 16, which is formed by a thin ring wall consisting of an inner cylindrical portion 17 and an outer, slightly conical portion 18 with an outwardly increasing cross-section. A ring-shaped slit 19 between the spout 14 and the ring-shaped wall 17, 18 allows some elastic compression thereof.

When such a hearing aid housing is to be adapted to the user's ear, such a coupling element of the invention as shown in FIG. 3 is placed on the hearing aid housing exit nipple formed by the spout 14 and the snap fastener means 16. The coupling element consists of a relatively flat housing with a ring-shaped side wall 20 and a circular end wall 21. The inner side of the ring-shaped wall 20 has a configuration with a cylindrical portion 20' and a conical portion 20" corresponding to the exterior of the snap fastener means 16 of the hearing aid housing 10 so that the coupling element housing can be pressed into locking engagement with the sound exit nipple of the hearing aid. The housing has a raised flange 22 at a location at the periphery from which a short spout 23 with a sound channel 24 extending through it projects. On the end wall 21 there is provided a raised portion 25 shaped as a segment of a cone, and this raised portion adjoins the flange 22 and forms the outward definition of a sound channel 26 which connects the interior of the housing with the spout channel 24. A tube section 27 has a short sleeve part 28, which forms an angle with the tube section and which can be applied to the spout 23 and be retained on it by friction in such a manner that the sleeve part can rotate on the spout, so that the orientation of the tube section with respect to the spout can be changed within certain limits determined by the angle between the sleeve part and the tube section.

In FIG. 4, the overall coupling element is shown as applied to the sound exit nipple of a hearing aid, and in FIG. 5 the aid with the coupling element is shown as applied to an ear plug 29 placed in an ear. Such an ear plug is usually custom made on the basis of a mould of the ear in question. During moulding of the ear plug the coupling element is placed in the mould and so positioned that—after adjustment of the spout—acoustic connection can be established between the end of the tube section 27 and the inner end of the ear plug part 30, which protrudes into the auditory canal, by a single, straight bore 31. Of course, the coupling element must additionally be so placed that its housing is open to the outer side of the ear plug so that the hearing aid housing can be detachably attached to the ear plug by snap engagement of the snap fastener means 16 in the coupling element housing during elastic compression of the ring-shaped wall 17, 18.

The angle formed by the tube section 27 with its sleeve part 28 may have other values than the one shown, and both the mounting of the tube section on the coupling element housing and the mounting of said housing on the hearing aid housing may be accomplished in other ways than those shown in the drawing and described in the foregoing.

I claim:

1. A coupling element for establishing acoustic connection between a hearing aid placed in the concha and having a substantially cylindrical housing (10) with a sound exit nipple (14) placed in the vicinity of the periphery of said housing, said housing being placed with the nipple facing inwardly into a custom moulded ear plug (29) placed in the auditory canal, characterized in that said coupling element consists of a substantially disc-shaped part (20), which is adapted to be detachably and rotatably attached to the nipple (14) of the hearing aid housing (10), a laterally directed spout (23) formed on said disc-shaped part for rotary movement with said disc-shaped part relative to said sound exit nipple, and an angularly bent tube section (27) rotatably mounted on said laterally directed spout.

* * * * *